United States Patent [19]

Shiells et al.

[11] Patent Number: 4,882,146

[45] Date of Patent: Nov. 21, 1989

[54] PREVENTING ADP-RIBOSYLATION OF G-PROTEINS IN A LIVING SUBJECT

[75] Inventors: Richard A. Shiells, Barwick Near Ware; Gertrude Falk, London, both of England

[73] Assignee: University College London, London, England

[21] Appl. No.: 174,407

[22] Filed: Mar. 28, 1988

[30] Foreign Application Priority Data

Mar. 26, 1987 [GB] United Kingdom ................. 8707293
Jun. 22, 1987 [GB] United Kingdom ................. 8714544

[51] Int. Cl.$^4$ ..................... A61K 31/52; A61K 31/44; A61K 31/195
[52] U.S. Cl. .................................. 424/10; 514/262; 514/355; 514/562
[58] Field of Search .................. 424/10; 514/356, 837, 514/355, 262, 562

[56] References Cited

U.S. PATENT DOCUMENTS 2,283,817  5/1942  Martin et al. ....................... 514/356
4,308,257 12/1981  Caspe .................................. 424/94.2

FOREIGN PATENT DOCUMENTS 1149318  4/1969  United Kingdom .
2029218  3/1980  United Kingdom .
2113524  8/1983  United Kingdom .
 215367  8/1985  United Kingdom .

OTHER PUBLICATIONS

Review of Medical Microbiology Jawetz et al., 11th edition, 1974, pp. 136–137.
Carroll et al.; Proceedings in Life Sciences; 1985, pp. 544–550; "ADP Ribosylation of Proteins".
Montanaro et al.; Arch. Sca. Boil., vol. 15, pp. 159–166; 1968; "Effect of Adenine and Nicotinamide on Amino Acid Incorporation of Cell-Free Systems . . . ".
Montanaro et al.; Biochem J., vol. 105, No. 2, pp. 635–640, 1967; "Binding of Nicotinamide-Adenine Dinucleotides to Diphtheria Toxin".
Goor et al.; J. Exp. Med. vol. 126, No. 5, pp. 923–939, 1967; "Studies on the Mode of Action of Diphtheria Toxin".
"Block of Light Responses of Salamander Rods by Pertussis Toxin and Reversal by Nicotinamide", G. Falk & R. A. Shiells, vol. 229, No. 1, pp. 131–134, FEBS Letters.
Guerrant, "Microbial Toxins and Diarrhoeal Disease" (Ciba Foundation Symposium 112, 1985, Pitman, London).
Goor et al., J. Exp. Med. 126 (1967), pp. 923–939.
Gill et al., "Microbial Toxins and Diarrhoeal Disease", Ciba Foundation Symposium 112, 1985, Pitman, London, pp. 57–69.

Primary Examiner—Douglas W. Robinson
Assistant Examiner—Raymond J. Henley, III
Attorney, Agent, or Firm—Cushman, Darby & Cushman

[57] ABSTRACT

Nicotinamide and its analogues (but not nicotinic acid) are effective in preventing or reversing the effects of microbial toxins, e.g. pertussis toxin, which ADP-ribosylate G-proteins.

3 Claims, No Drawings

PREVENTING ADP-RIBOSYLATION OF G-PROTEINS IN A LIVING SUBJECT

This invention relates to preventing and reversing adenosine diphosphate (ADP)-ribosylation of G-proteins by microbial toxins.

Proteins which bind guanosine triphosphate (GTP), so-called G-proteins, are important in many physiological systems and are usually associated with some form of signal transduction or protein synthesis. It is known that the toxic effects of some bacterial toxins (called "ADP-ribosylating toxins") are associated with the ADP-ribosylation (ADPR) of G-proteins which is catalysed by the toxins. Pathological effects associated with cholera, diphtheria, whooping cough (pertussis) and pathological strains of *Escherichia coli* and Pseudomonas involve ADP-ribosylation of G-proteins. The consequences of G-protein ADPR differ for each toxin and the particular G-protein affected. Cholera toxin causes the secretory diarrhoea characteristic of cholera by activating a G-protein linked to adenylate cyclase. This long-lasting or "permanent" activation causes accumulation of cyclic adenosine 3',5'-monophosphate (cAMP) in cells of the intestinal mucosa, and this increase in cAMP leads to increased secretion. In vitro, the cholera toxin can activate adenylate cyclase in virtually all vertebrate cells. Pertussis toxin inactivates G-proteins. This toxin acts selectively, however, on an inhibitory subunit of the adenylate cyclase G-protein. ADPR of this site also leads to activation of adenylate cyclase. It is not known exactly how the characteristic whooping cough arises in pertussis infection; it may be caused by increased secretion of pulmonary epithelial cells or by some effect of the toxin on C.N.S. neurons. Diphtheria and *Pseudomonas* toxins ADP-ribosylate the G-protein "elongation factor 2" causing inactivation, and thereby inhibiting protein synthesis. The ADP-ribosylating toxin of *E. coli* has a similar action to cholera toxin.

It has now been discovered that the ADPR of G-proteins can be prevented or reversed by nicotinamide and its analogues, except nicotinic acid which is ineffective. The importance of nicotinamide in nutrition, e.g. in preventing the disease pellagra, is well known, but for this purpose only low (ca. 10 mg) doses of nicotinamide are required. The desirable therapeutic effects obtained with the present invention require the use of a much larger amount of nicotinamide or one of its analogues.

The valuable effect of nicotinamide has been demonstrated in the following way. Photo-activation of rhodopsin in retinal rods, which may be studied in retinal slices, activates a G-protein (transducin). ADPR of this G-protein by pertussis toxin results in its stabilization in an inactive state, leading to depolarization and block of light responses of the rods. Perfusion of the retinal slice with 0.1–10 mM nicotinamide is effective in reversing ADP-ribosylation of transducin, as indicated by the recovery of light responses and membrane potential. Subsequent applications of pertussis toxin are ineffective in blocking light response in the presence of nicotinamide, and thus demonstrate the prevention of ADPR of a G-protein in an intact cell which would normally have been catalysed by the bacterial toxin.

ADP-ribosylating toxins are known to catalyse the reaction:

NAD + G-protein = G-protein-ADPR + nicotinamide + H+ where  NAD = nicotinamide adenine dinucleotide and ADPR = ADP-ribose. Bacterial toxins such as pertussis toxin and cholera toxin drive this reaction to the right. However, by providing a high concentration of nicotinamide, the reaction can be driven to the left and the G-protein thus restored to its normal functional state. The precise mechanism by which nicotinamide is effective in blocking ADPR is not fully understood. There is evidence that it directly competes with AND for AND-binding sites on the toxin molecule.

The efficacy of nicotinamide in the reversal of ADPR of G-proteins by microbial toxins is not evident from published biochemical data. This is due to two reasons:

(1) The intracellular concentrations of free substrate AND have been over-estimated. This has led to the assumption that under natural conditions the above reaction is driven entirely to the right, and thus has lead to the commonly held misconception that ADPR by bacterial toxins is irreversible except at very high concentrations (at least 50 mM) of nicotinamide.

(2) Endogenous ADP-ribosyltransferases, particularly in retinal rods and in the adenylate cyclase system of rat adipocytes, have only recently been discovered. Rapid endogenous turnover of G-protein ADPR indicates the presence of endogenous enzymes catalysing the reverse reaction:

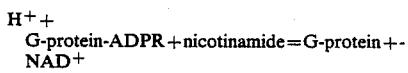

In the exploitation of the present invention, this reaction is driven to the right by providing increased substrate nicotinamide, or analogue thereof, which restores G-protein function. Such ADPR-G-protein cleavage enzymes have been isolated from erythrocytes. The presence of such enzymes in the intact cell increases the efficacy of nicotinamide over that to be expected from biochemical data using isolated G-proteins.

Accordingly, the present invention provides a method of reversing and/or blocking the effects of bacterial toxins which ADP-ribosylate G-proteins by administering to a subject endangered by such a bacterial toxin an effective amount of nicotinamide or analogue thereof (excluding nicotinic acid). The invention further provides nicotinamide and its analogues (excluding nicotinic acid) for use in producing a pharmaceutical composition for the therapy of pathological conditions caused by ADP-ribosylating microbial toxins. Suitable analogues of nicotinic acid include, for example, isonicotinamide and N-methyl-nicotinamide.

The toxicity of nicotinamide is low, and relatively large amounts may be administered without toxic effect. Administration with methionine, to prevent toxicity due to methylation of nicotinamide, is recommended. The co-administration of other compounds such as adenine which also inhibit ADP-ribosylation of G-proteins may also be beneficial. Strategies to limit drug concentrations to affected regions alone should preferably be employed, e.g. to the lower intestine in cholera (by coating pills), and to the lungs in pertussis (by aerosol). For the purposes of the present invention a daily oral dose of 1 to 5g for a standard 70 Kg adult is appropriate or, if desired, a daily intravenous dose of 0.2 to 1 g, e.g 0.5 g, may be administered. Methionine may be administered in substantially the same dosage and by the same routes. If adenine is administered, an appropriate dosage is about one tenth of the dosage of the nicotinamide.

Diseases associated with bacterial toxins having ADPR activity include cholera, whooping cough, diphtheria, and gastritis caused by pathogenic forms of *E. coli.* Evidence is emerging that ADP-ribosylation is a common mechanism by which many bacterial and viral-produced toxins operate. In each case, pathogenic effects are caused by ADP-ribosylating toxins produced by the micro-organism. The present invention provides a means for counteracting such toxic effects and thereby enabling the host's normal defense mechanisms to build u and meet the infection.

We claim:

1. A method of reversing or blocking the adverse effects in a living subject of a microbial toxin which ADP-ribosylates G-group which comprises administering to said subject endangered by said microbial toxin an amount of nicotinamide effective to reverse or block said adverse effect.

2. The method according to claim 1 wherein the nicotinamide is administered with a substantially equal dose of methionine, a dose of adenine in an amount substantially equal to 1/10th of the dose of nicotinamide, or with both.

3. A method according to claim 1 wherein the said microbial toxin is a toxin produced by microbes causative of cholera, diptheria, or pertussis or by a patholoigical strain of *Escherichia coli* or Pseudomonas.

* * * * *